(12) United States Patent
Schaefer

(10) Patent No.: US 8,772,723 B2
(45) Date of Patent: Jul. 8, 2014

(54) OPTICAL GAS SENSOR DEVICE AND METHOD FOR DETERMINING THE CONCENTRATION OF A GAS

(71) Applicant: Frank Schaefer, Tuebingen (DE)

(72) Inventor: Frank Schaefer, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/015,122

(22) Filed: Aug. 30, 2013

(65) Prior Publication Data

US 2014/0091219 A1     Apr. 3, 2014

(30) Foreign Application Priority Data

Sep. 4, 2012 (DE) .......................... 10 2012 215 660

(51) Int. Cl.
    *G01J 5/58*     (2006.01)
(52) U.S. Cl.
    USPC ..................................... 250/339.13; 250/343
(58) Field of Classification Search
    USPC ........................................... 250/338.1, 338.5
    See application file for complete search history.

(56) References Cited

U.S. PATENT DOCUMENTS 8,053,728 B2    11/2011 Chrzan
8,330,957 B2 *  12/2012 Hager ........................... 356/438
2007/0246653 A1 * 10/2007 Zhou ........................... 250/339.1
2011/0042570 A1 *  2/2011 Wong ............................. 250/340
2013/0075615 A1 *  3/2013 Starta et al. ................. 250/341.7

FOREIGN PATENT DOCUMENTS

| DE | 4434814 | 4/1996 |
| DE | 19713928 | 4/1998 |
| DE | 19929034 | 12/2000 |
| DE | 102004044145 | 4/2006 |
| JP | 21008096228 | 4/2008 |

* cited by examiner

*Primary Examiner* — Mark R Gaworecki
(74) *Attorney, Agent, or Firm* — Kenyon & Kenyon LLP

(57) ABSTRACT

A gas sensor device for determining a molar concentration of a gas to be detected, that absorbs light of a measurement wavelength that is characteristic of the gas in the infrared light region, includes a light emission device emitting measurement light of measurement wavelength into a solid angle region of a light absorption path extending through the gas, and a light detector measuring an intensity of at least one component of the measurement light that has propagated through the light absorption path, the light absorption path extending from the light emission device to an object outside the gas sensor device that at least partially reflects the measurement light to the light detector, and being essentially disposed outside of the gas sensor device, and means for determining the length of the light absorption path. A method for determining a concentration of a gas to be detected is also described.

15 Claims, 4 Drawing Sheets

OPTICAL GAS SENSOR DEVICE AND METHOD FOR DETERMINING THE CONCENTRATION OF A GAS

CROSS REFERENCE TO RELATED APPLICATION

The present application claims priority to Application No. DE 10 2012 215 660.7, filed in the Federal Republic of Germany on Sep. 4, 2012, which is expressly incorporated herein in its entirety by reference thereto.

FIELD OF INVENTION

The present invention relates to an optical gas sensor device and to a method for determining the concentration of a gas.

BACKGROUND INFORMATION

Known gas sensors are mostly based on chemical or optical sensing principles. For the most part, optical sensing principles employ an absorption process, as summarized in FIG. 4. The known infrared optical gas sensor 2 shown exemplarily in FIG. 4 is based on the principle whereby, in a gas mixture, such as air, in which the concentration of a gaseous component is to be measured, for instance, the $CO_2$- concentration in the air, the gaseous component to be measured absorbs light at a characteristic wavelength of $\lambda_{gas}$ in the infrared spectral region. If, in the case of light, which has propagated through gas 7, respectively the gas mixture along an absorption path 12, the light intensity at this characteristic wavelength $\lambda_{gas}$ is compared to the light intensity at reference wavelength $\lambda_{ref}$ that is adjacent to the characteristic wavelength, that is not absorbed by the gaseous component to be measured, then the concentration of the gaseous component to be measured can be calculated on the basis of the known Lambert-Beer law of light absorption, as follows:

$$I=I_0 * \exp(-\epsilon * c * L) \quad \text{Equation 1}$$

I=the light intensity given an absorption of $[W/m^2]$
$I_0$=the intensity without absorption $[W/m^2]$
$\epsilon$=the molar absorption coefficient $[m^2/mol]$(gas-dependent, wavelength-dependent and temperature-dependent)
c=the molar concentration $[mol/m^3]$; and
L=the length of the absorption path 12 [m].

To calculate the molar concentration c of the gas to be detected, Equation 1 requires knowing the known molar absorption coefficient $\epsilon$, a measured value for the light intensity I with absorption (i.e., at the characteristic wavelength $\lambda_{gas}$), a measured value for the light intensity $I_0$ without absorption (i.e., at the reference wavelength $\lambda_{ref}$), and a measured value for the length L of the absorption path 12. The longer the absorption path 12 is, the more light that is absorbed, and the lower the molar gas concentration c that can be measured.

The basic design of an infrared optical gas sensor 2 shown exemplarily in FIG. 4 for measuring the concentration of $CO_2$ in air, for example, includes a light source 10 that is broadband emitting in the infrared spectral region and whose emission spectrum includes the wavelength $\lambda_{gas}$ that is characteristic of the gas $CO_2$ to be measured, and a wavelength $\lambda_{ref}$ adjacent thereto at which the gas mixture (the air) does not absorb, and, in addition, a light detector 80 having at least two measuring channels for measuring the light intensity at the wavelength $\lambda_{gas}$ that is characteristic of the gas component to be measured (also referred to herein as measurement wavelength), and at the reference wavelength $\lambda_{ref}$. The light detector 80 includes a filter device 83 for allowing light of measurement wavelength $\lambda_{gas}$ to pass through, and a measuring light detector 81 disposed downstream therefrom, a filter device 84 for allowing light of reference wavelength $\lambda_{gas}$ to pass through, and a reference light detector 82 disposed downstream therefrom.

The purpose of the first measuring channel 88 of the light detector 80 is to measure the light intensity I remaining at measurement wavelength $\lambda_{gas}$ following propagation through the absorption path 12. The purpose of the second measuring channel 89 is to measure the light intensity $I_0$ that has passed through at wavelength $\lambda_{ref}$, where the gas mixture does not exhibit any absorption. The absorption spectrum of the gas mixture (air) is shown exemplarily in the lower portion of FIG. 4. One can discern that the gas components $H_2O$, $CH_4$, $CO_2$ and CO contained in the gas mixture exhibit a pronounced light absorption (relative absorption) at different wavelengths that are characteristic of the particular gas components. The upper horizontal axis of the absorption spectrum illustrated in the lower portion in FIG. 4 indicates the wavelength $\lambda$, expressed in micrometers [μm], of the infrared light; and the lower horizontal axis indicates the corresponding wave number, which is defined as the reciprocal value $1/\lambda$ of the wavelength, measured in $[10^5 \text{ cm}^{-1}]$.

Thus, infrared optical gas sensors are known where the measurement path, respectively the absorption path is configured within the gas sensor, in particular within a housing of the gas sensor. To achieve a longest possible absorption path between the infrared light source and the light detector, the gas sensor includes at least one reflector device allowing it to realize a plurality of absorption path sections within the gas sensor, as in the case of the photometric gas sensor described in the German Patent Application No. DE 10 2004 044 145.

It is a characteristic of the known optical infrared gas sensors that, in spite of a sophisticated reflector device design, the entire absorption path is limited by the dimensions of the gas sensor. Thin, portable devices, such as cell phones, handheld measuring devices or laser distance measurement devices, in particular, have no available space for realizing such an absorption path lengthened by a reflector device therein.

SUMMARY

A gas sensor device and a method for determining a molar concentration of a gas to be detected are achieved according to advantageous exemplary embodiments of the present invention.

In accordance with one exemplary aspect of the present invention, the measurement light from the light emission device is emitted into a spatial region located outside of the gas sensor device, and the light detector detects an intensity of measurement light that has been reflected off an object located in this spatial region. Thus, the measurement path is essentially disposed outside of the gas sensor device according to the present invention and may be on the order of one meter or more in length and, in any case, many times longer than in conventional optical infrared gas sensors where the measurement path extends within a housing of the gas sensor and is typically on the order of centimeters in length. The much longer measurement path makes it possible to achieve a substantially greater sensitivity for determining the molar concentration of the gas to be detected than that provided by conventional optical infrared gas sensors. Also, the gas sensor device according to the present invention does not contain or require any device-internal reflector device and may, therefore, have a spatially smaller, respectively more space saving design than conventional optical infrared gas sensors. Thus, the gas sensor device according to the present invention may be integrated relatively simply in a portable device, such as a cell phone, a handheld measuring device, a camera, or laser distance measurement device, in which space constraints had precluded existing optical infrared gas sensors.

In accordance with one exemplary embodiment, an optical gas sensor device is provided for determining a molar concentration of a gas to be detected, the gas absorbing light of a measurement wavelength that is characteristic of the gas to be detected and not absorbing light of a predetermined reference wavelength that differs from the measurement wavelength, and the measurement wavelength and the reference wavelength residing in the region of infrared light. In this gas sensor device:

the light emission device is designed for emitting measurement light of the measurement wavelength and reference light of the reference wavelength into a solid angle region that encompasses a spatial region located outside of the gas sensor device;

the light detector is designed for measuring an intensity of measurement light that has been reflected off of an object located in the spatial region, and an intensity of reference light that has been reflected off of an object located in the spatial region.

Another exemplary embodiment includes means for determining the length of the light absorption path from the light emission device to the object and, from there, to the light detector.

According to another exemplary development, if the light emission device is designed for emitting measurement light at a first point in time and at a second point in time into a solid angle region that encompasses a first and second spatial region located outside of the gas sensor device;

the light detector is then designed for measuring a first intensity of measurement light that has been reflected off of a first object located in the first spatial region at a first distance from the gas sensor device at, respectively subsequently to the first point in time, and for measuring a second intensity that has been reflected off of a second object located in the second spatial region at a second distance from the gas sensor device, at, respectively subsequently to the second point in time; and the means for determining the length of the light absorption path then include means for determining a difference between a first propagation path of the light from the light emission device to the first object and, from there, to the light detector, and a second propagation path of the light from the light emission device to the second object and, from there, to the light detector.

The first object and the second object may also be the same object. For purposes of the measuring operation, it is located at a first point in time at a first distance and, at a second point in time, at a second distance from the gas sensor device.

The object, respectively the first and the second object, may be a wall. The wall is irradiated by the measurement light, respectively by the reference light, preferably substantially orthogonally or virtually orthogonally to the wall surface thereof. A wall provides a large reflecting surface area and is able to reflect an especially large amount of measurement light back in the direction of the light detector.

In a first exemplary variant, the light emission device may be a broadband light source that is designed for emitting light in a broadband spectral region that includes the measurement wavelength and the reference wavelength. In addition, the light detector may include two measuring channels and be designed for performing a measurement in the first measuring channel of an intensity of measurement light that has been reflected off of an object located in this spatial region, and for performing a measurement in the second measuring channel of an intensity of reference light that has been reflected off of an object located in the spatial region. This exemplary embodiment employs a broadband light source that may be relatively inexpensive.

The light source may include means for bundling the light emitted therefrom into the solid angle region. The bundling means may include a converging lens and/or a reflector device having an at least substantially concave reflector. In the solid angle region containing the reflecting object, the bundling means increase the intensity of the light incident to the object and, thus, the measurement light intensity measurable by the light detector, which, in turn, enhances the measurement accuracy in comparison to an exemplary embodiment that does not include bundling means.

The first measuring channel of the light detector may include a first filter device that is designed for essentially transmitting only light in a first narrowband measurement spectral region that essentially includes the measurement wavelength and not the reference wavelength. In addition, the second measuring channel of the light detector may include a second filter device that is designed for essentially transmitting only light in a second narrowband reference spectral region that essentially includes the reference wavelength and not the measurement wavelength. The filters block light that is not needed for a particular measurement, thereby improving the ratio of detected measurement light to scattered light, respectively to the noise signal of the light detector, and thus the intensity measuring sensitivity thereof.

In a second exemplary variant, the light emission device may be a measurement light source that is designed for emitting measurement light in a narrowband measurement spectral region that essentially includes the measurement wavelength and not the reference wavelength, and a reference light source that is designed for emitting reference light in a narrowband reference spectral region that essentially includes the reference wavelength and not the measurement wavelength. The light detector may be designed for measuring an intensity of measurement light that has been reflected off of the object located in the spatial region and an intensity of reference light that has been reflected off of the object located in the spatial region. This exemplary embodiment employs narrowband light sources, the total light intensity emitted by the light source being limited to the narrow wavelength band, and, overall, therefore, being able to be substantially lower than that from the broadband light source. For that reason, the narrowband light source may be operated more energy efficiently than the broadband light source.

The measurement light source may be a first laser device that is designed for emitting a first measurement light beam, and the reference light source may be a second laser device that is designed for a emitting a reference light beam. The exemplary embodiment of the measurement light source and the reference light source as a laser device makes possible a very high level of directivity of the measurement light beam and the reference light beam, so that a relatively small object suffices for reflecting the measurement light to the light detector during the measurement.

Another preferred exemplary embodiment provides means for determining the molar concentration of the gas to be detected that are designed for calculating the molar gas concentration on the basis of the ratio of the measurement light intensity measured by the light detector and the reference light intensity measured by the light detector, as well as the propagation path of the light. Accordingly, in accordance with the second exemplary aspect of the present invention, the gas sensor may include means for determining the molar gas concentration of the gas to be detected that are designed for calculating the molar gas concentration on the basis of the ratio of the first measurement light intensity measured by the light detector that has traversed the first propagation path, and of the second measurement light intensity measured by the light detector that has traversed the second propagation path, as well as the difference between the first propagation path and the second propagation path. These exemplary embodiments render superfluous the need for a device, such as a pocket computer or a PC, to supplement the gas sensor device, for calculating the molar gas concentration from the parameters measured by the gas sensor device (ratio of the light intensities and propagation path, for example, the difference in the propagation path of the light).

A light emission device of the type in question may be designed for emitting light in one or more light pulses. The modulation of the light irradiated by the light emission device in the form of light pulses makes it possible for a lock-in amplifier to be used in the light detector that achieves a higher signal-to-noise ratio and thus a higher measuring accuracy than an amplifier that does not employ lock-in technology. The modulation of the light in the form of light pulses also makes it possible for the propagation path of the light to be determined by measuring the propagation time of the light pulse(s). In the case of the light intensity measurements, an influence of the ambient brightness may also be suppressed, respectively eliminated from the calculation.

To modulate the light that is in the form of light pulses, the light emission device may include a controllable optical shutter device having a transmission propagation path that may be blocked and cleared in a controllable temporal sequence. Alternatively, a controllable temporal sequence of a pulsating power supply may be used to operate the light emission device.

In the gas sensor device in accordance with the second exemplary variant, the measurement light source may be designed for emitting one or a plurality of measurement light pulses, and the reference light source for emitting one or a plurality of reference light pulses, a particular measurement light pulse and a particular reference light pulse being temporally offset from one another. This exemplary embodiment of the modulation makes it possible for a lock-in amplifier having a high signal-to-noise ratio and thus a higher measuring accuracy to be used in the light detector, both for detecting the measurement light, as well as the reference light, and for the propagation path of the light to be determined by measuring the propagation time, both of the measurement light pulses, as well as of the reference light pulses.

The means for determining the propagation path, respectively the means for determining the difference between the first propagation path and the second propagation path in the gas sensor device may at least include a means that is selected from a group which includes:

- an input device designed for inputting the distance between the gas sensor device and the object that corresponds to the propagation path, respectively for the inputting of the propagation path by an operator of the gas sensor device;
- a distance measuring device designed for generating a signal that is indicative of the distance between the gas sensor device and the object that corresponds to the propagation path, it being possible for the distance measuring device to include, in particular, an auto-focus device of a camera;
- means for determining the propagation path of the light emitted by the light emission device as light pulses, on the basis of a measurement of the propagation time of at least one light pulse;
- a laser distance measurement device that is designed for determining the distance on the basis of a frequency modulation of a light emitted by a laser light source and an interference produced by this light; and
- triangulation means for determining the distance, the means including, in particular, a laser device that is provided separately for the gas sensor device, and a camera that is mechanically coupled to the gas sensor device.

The means for determining the difference between the first propagation path and the second propagation path of the light may include an accelerometer that is designed for measuring the acceleration of the gas sensor device along the path thereof from a first position at the first point in time to a second position at the second point in time, and means for calculating a two-times integration of the acceleration measured by the accelerometer as a function of the time from the first point in time to the second point in time.

The aforementioned exemplary embodiments of the means for determining the propagation path, for example, the propagation path difference, make it possible for these means to be integrated, together with the remaining components of the gas sensor device, in one single portable device, for instance, a cell phone, a handheld measuring device, a laser distance measurement device or a camera.

In addition, the gas sensor device in accordance with the present invention may include a pressure sensor for measuring the barometric air pressure. The gas sensor device may also include means for determining the concentration of the gas to be detected on the basis of the specific molar concentration of this gas and the barometric air pressure measured by the pressure sensor.

The gas sensor device in accordance with the present invention may be configured to be part of a portable device, for instance, a cell phone, a handheld measuring device, a laser distance measurement device or a camera.

The gas sensor device in accordance with the present invention may be used in a method for determining a molar concentration of a gas to be detected, the gas absorbing light of a measurement wavelength that is characteristic of the gas to be detected, respectively not absorbing light of a predetermined reference wavelength that differs from the measurement wavelength, and the measurement wavelength, respectively the reference wavelength, residing in the infrared light region.

Exemplary embodiments of the present invention are described in the following with reference to the accompanying drawings.

DETAILED DESCRIPTION

Figure 1:
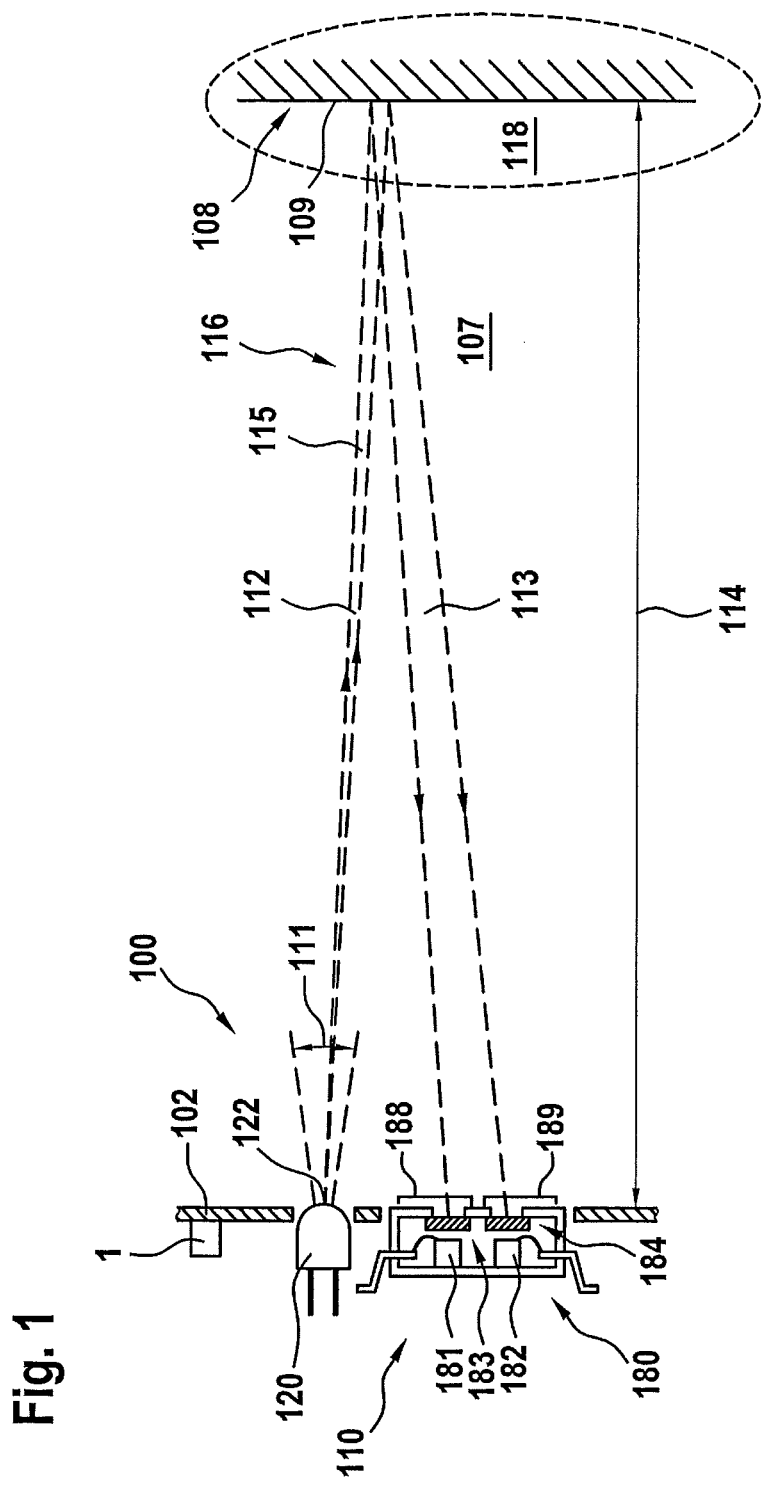
FIG. 1 is a schematic representation of a gas sensor device in accordance with a first exemplary variant of a first exemplary embodiment of the present invention.

In the exemplary embodiment shown in FIG. 1, a gas sensor device 100 in accordance with the first exemplary variant of the first exemplary embodiment of the present invention includes a light emission device 110 that is designed for emitting measurement light of measurement wavelength $\lambda_{gas}$ and reference light of reference wavelength $\lambda_{gas}$ into a solid angle region 111 that encompasses a spatial region 118 located outside of gas sensor device 100, light detector 180 that is designed for measuring an intensity of measurement light that has been reflected off of an object 108 located in spatial region 118, and an intensity of reference light that has likewise been reflected off of object 108 located in spatial region 118. A bundle of rays 115 of light 116 emitted into solid angle region 111 traverses gas 107, initially along propagation path 112 from light emission device 110 to object 108, is partially reflected off of object 108, and again traverses gas 107 along propagation path 113 from object 108 to light detector 180. In the example of FIG. 1, reflecting object 108 is a wall 109 that is disposed at a distance 114 from gas sensor device 100.

Light emission device 110 and light detector 180 are disposed in relatively close mutual proximity, i.e., at a relatively very small distance from one another in comparison to distance 114 between gas sensor device 100 and object 108. Therefore, it holds, at least approximately, that the absorption path of the light, which includes propagation path 112 from light emission device 110 to object 108 and second propagation path 113 from object 108 to light detector 180, is equal to twice distance 114 between gas sensor device 100 and object 108. This approximation also applies to the exemplary embodiments of a gas sensor device 200, 300 illustrated in FIGS. 2 and 3, as well as to the general principle of the present invention described herein.

Light emission device 110 shown in FIG. 1 is a broadband light source 120, that is designed for emitting light in a broadband spectral region that includes measurement wavelength $\lambda_{gas}$ and reference wavelength $\lambda_{ref}$. Light source 120 is a diode (LED), for example, that emits light in the infrared range. In addition, light source 120 may include means (not shown) for bundling the emitted light into solid angle region 111. These bundling means may be configured as a converging lens (not shown) and/or as a reflector device (not shown) having at least one substantially concave reflector.

Light detector 180 shown in FIG. 1 includes two measuring channels 188, 189. The purpose of first measuring channel 188, respectively second measuring channel 189, is to measure an intensity I of measurement light, respectively an intensity $I_0$ of reference light, (see equation 1) that has been reflected off of object 108. First measuring channel 188 of light detector 180 includes a first filter device 183 that is designed for essentially transmitting only light in a first narrowband measurement spectral region that includes measurement wavelength $\lambda_{gas}$ and not reference wavelength $\lambda_{ref}$. Second measuring channel 189 of light detector 180 includes a second filter device 184 that is designed for essentially transmitting only light in a second narrowband reference spectral region that includes reference wavelength $\lambda_{ref}$ and not measurement wavelength $\lambda_{gas}$. First measuring channel 188 includes, in addition, a first photodetector, respectively measuring light detector 181, configured downstream of filter device 183, and second measuring channel 189 includes a second photodetector, respectively reference light detector 182, configured downstream of filter device 184. First photodetector 181, respectively second photodetector 182, each output a signal that is indicative, preferably proportional, to intensity I of the measurement light, respectively intensity $I_0$ of the reference light. The signals are fed to a signal evaluation unit (not shown), and converted into measured values for corresponding light intensities I, respectively $I_0$.

In addition, gas sensor device 100 shown in FIG. 1 includes means 1 for determining the length of light absorption path 112, 113 of measurement light, respectively reference light, from light emission device 110 to light detector 180. As is readily apparent in FIG. 1, light absorption path 112, 113 is essentially disposed outside of gas sensor device 100. This applies correspondingly to the exemplary embodiments of a gas sensor device 200, respectively 300, shown in FIGS. 2 and 3.

Figure 2:
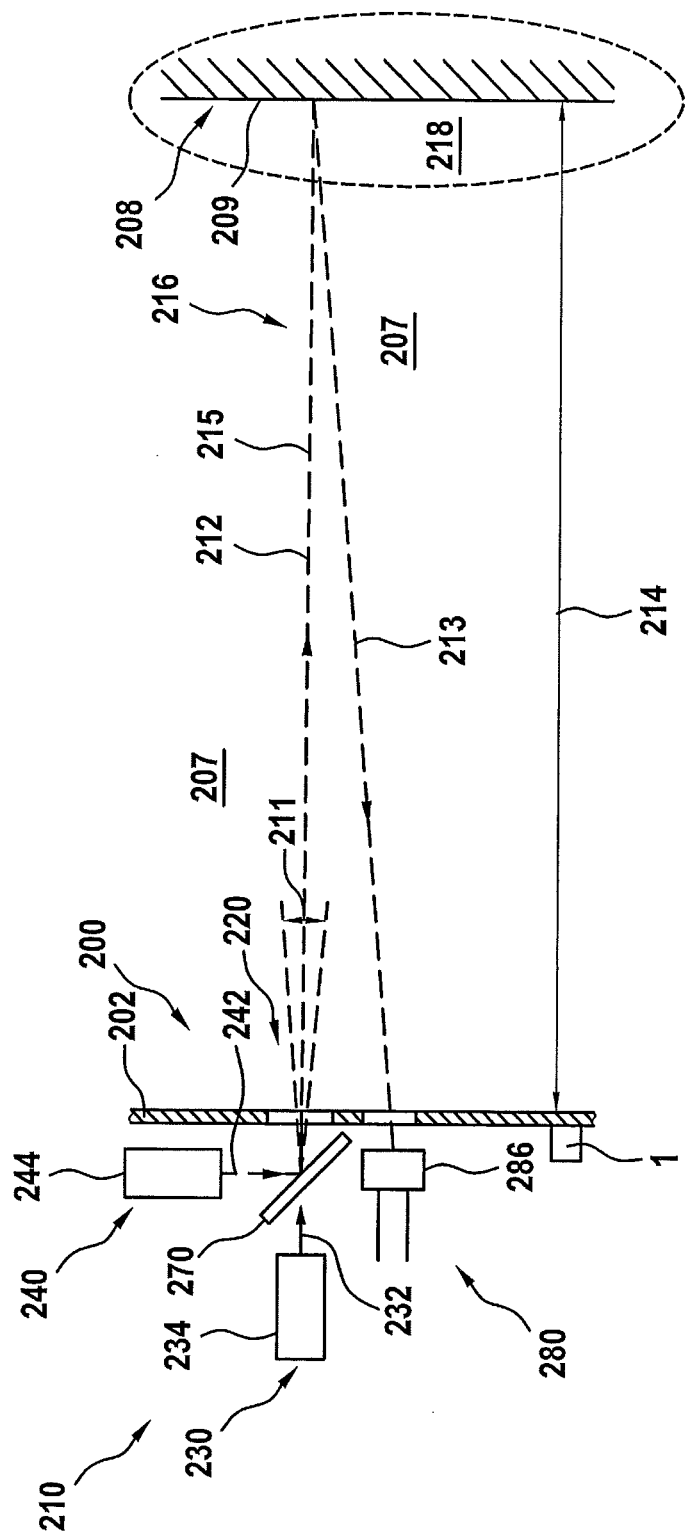
FIG. 2 is a schematic representation of a gas sensor device in accordance with a second exemplary variant of a first exemplary embodiment of the present invention.

The exemplary embodiment of a gas sensor device 200 shown in FIG. 2 differs from the exemplary embodiment of gas sensor device 100 shown in FIG. 1 essentially by the embodiment of light emission device 210 and of light detector 280.

Light emission device 210 of gas sensor device 200 shown in FIG. 2 includes a measurement light source 230 that is designed for emitting measurement light in a narrowband measurement spectral region, which essentially contains measurement wavelength $\lambda_{gas}$ and not reference wavelength $\lambda_{ref}$ into a solid angle region 211, and a reference light source 240 that is designed for emitting reference light in a narrowband reference spectral region, which essentially includes reference wavelength $\lambda_{ref}$ and not measurement wavelength $\lambda_{gas}$. Reference light source 240 is designed as a second laser device 244 that emits a reference light beam 242. In addition, light emission device 210 includes a beam combiner 270 that is configured, for example, as a semitransparent, plane-parallel plate that is positioned in the ray paths of measurement light beam 232 and of reference light beam 242 in a way that superposes the same to form a ray bundle 215. In accordance with the exemplary embodiment shown in FIG. 1, the measurement light and the reference light traverse gas 207 in the exemplary embodiment shown in FIG. 2 as well, along a first propagation path 212 from light emission device 200 to object 208, and, after being reflected off of object 208, along a second propagation path 213 from object 208 to light detector 280.

Light detector 280 is designed for measuring an intensity I of measurement light and an intensity $I_0$ of reference light that has been reflected in each case off of object 208. In the exemplary embodiment shown in FIG. 2, there is no need for narrow-band filter devices, such as filter devices 183 and 184 in light detector 180 in FIG. 1, for instance. This is because the wavelengths are selected, respectively measurement wavelength $\lambda_{gas}$ and reference wavelength $\lambda_{ref}$ are specified, on the basis of the narrowband characteristic of the light emitted by first laser device 234 (measurement light laser) and second laser device 244 (reference light laser). Accordingly, light detector 280 is designed as an infrared light detector 286 that is sensitive in the infrared spectral region and whose spectral sensitivity is substantially constant in a spectral region containing measurement wavelength $\lambda_{gas}$ and reference wavelength $\lambda_{ref}$.

With respect to the Beer-Lambert law of light absorption (Equation 1), it holds that, in the case of the measurement by two-channel light detector 180 of gas sensor device 100 shown in FIG. 1, just as in the case of the measurement that employs two narrowband spectral regions, respectively two laser wavelengths $\lambda_{gas}$ and $\lambda_{ref}$ in the case of gas sensor device 200 shown in FIG. 2, I is the light intensity measured by light detector 180, 280 at measurement wavelength $\lambda_{gas}$, and $I_0$ is the light intensity measured by light detector 180, 280 at reference wavelength $\lambda_{ref}$. Transposing Equation 1 yields:

$$c = -\ln(I/I_0)/(\epsilon * L) \quad \text{Equation 2,}$$

L being twice distance 114, 214 between gas sensor device 100, 200 and object 108, 208. Equation 2 describes the calculation rule for calculating the molar gas concentration c from measured light intensities I and $I_0$ at the measurement wavelength, respectively the reference wavelength, the known specific molar absorption coefficient ε for the gas to be detected, and length L of the absorption path.

Figure 3:
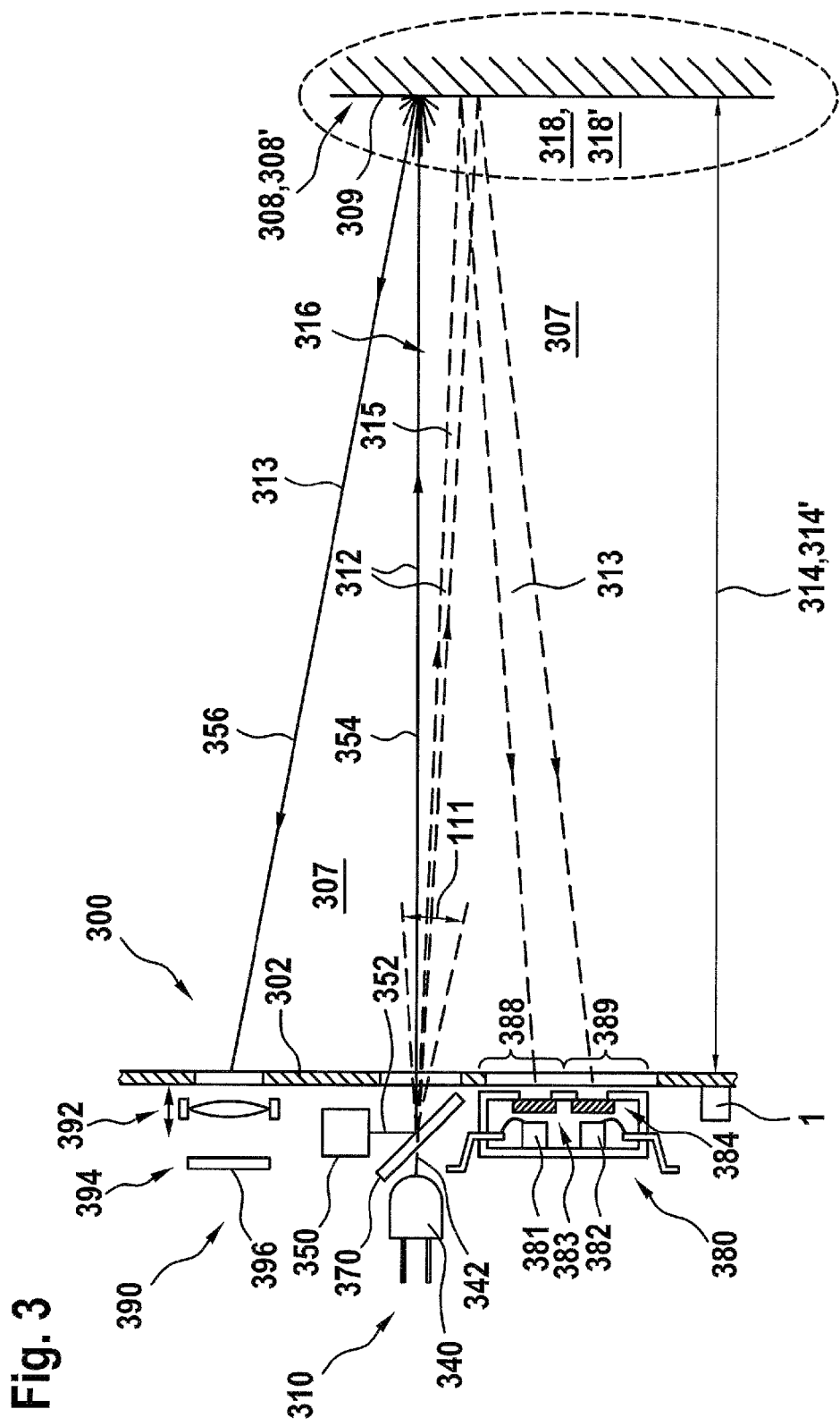
FIG. 3 schematically illustrates a gas sensor device in accordance with a second exemplary embodiment of the present invention.
Figure 4:
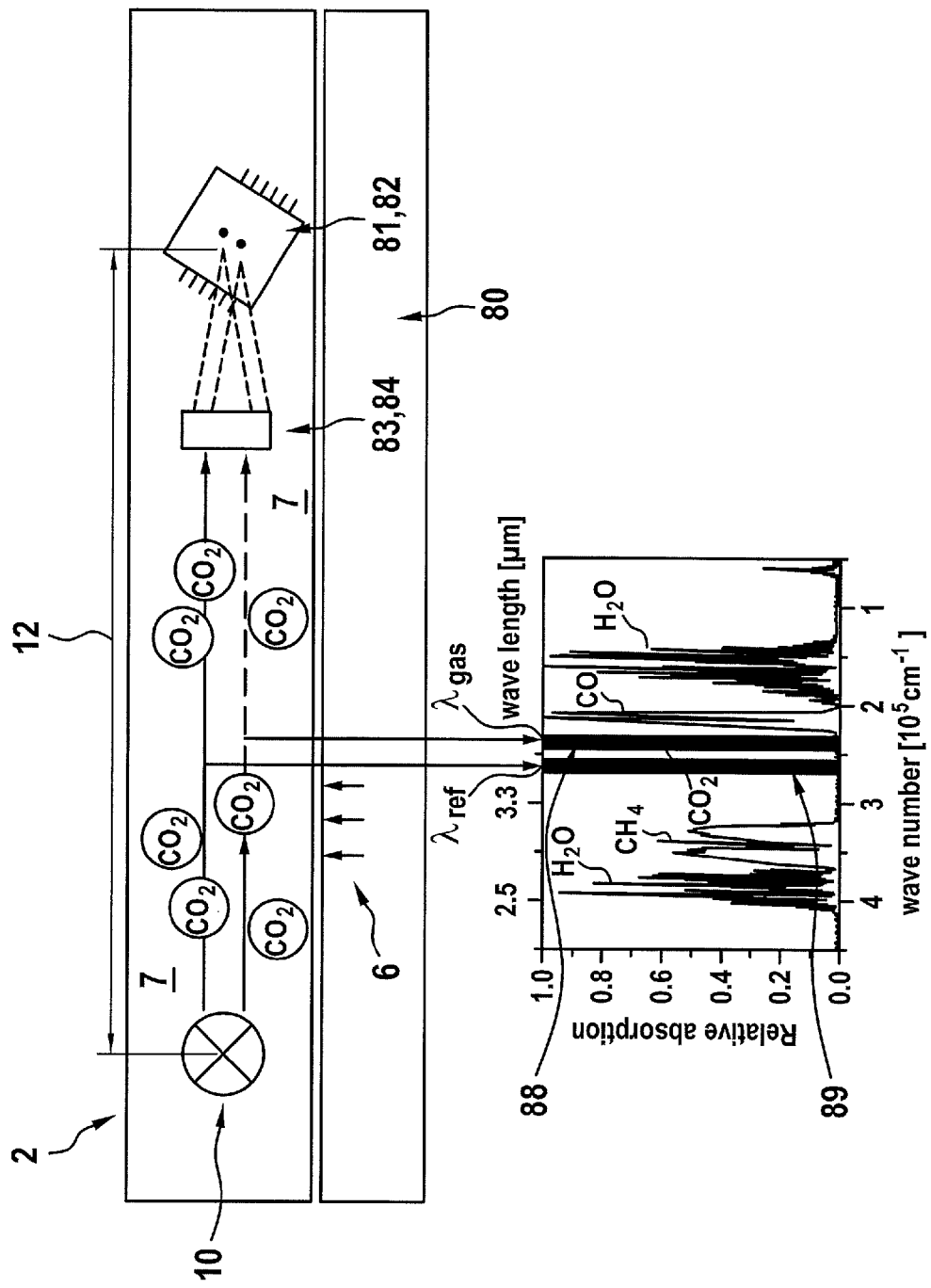
FIG. 4 is a schematic representation of an embodiment of a known infrared optical gas sensor.

In the case of the exemplary embodiment of a gas sensor device 300 shown in FIG. 3, the measuring principle for molar gas concentration c differs from the previously described measuring principle implemented in gas sensor devices 100, 200 from FIGS. 1 and 2 in that the light intensities are not realized at two different wavelengths (measurement wavelength $\lambda_{gas}$ and reference wavelength $\lambda_{ref}$); rather two light intensity measurements are performed in a narrowband spectral region that contains measurement wavelength $\lambda_{gas}$ for two different propagation paths, respectively two light absorption paths of different lengths (i.e., for two different distances 314, 314' of gas sensor device 300 from reflecting object 308).

Starting out from Equation 1, it holds for two measurements at two different absorption paths $L_1$ and $L_2$, which are implemented at measurement wavelength $\lambda_{gas}$, that:

$$I_1 = -I_0 * \exp(-\epsilon * c * L_1)$$

$$I_2 = -I_0 * \exp(-\epsilon * c * L_2) \quad \text{Equation 3}$$

The two aforementioned equations may be solved for $I_0$ and equated. It may then be solved for c, so that the following calculation instruction is derived for calculating molar concentration c:

$$c = \ln(I_1/I_2)/(\epsilon * L_{21}) \text{ where } L_{21} = L_2 - L_1 \quad \text{Equation 4}$$

In accordance with Equation 4, besides the ratio of intensities $I_1$ and $I_2$ measured for the two different absorption paths $L_1$ and $L_2$ (which are generally temporally offset from one another), difference $L_{12}$ between two absorption paths $L_1$ and $L_2$ is also needed to calculate molar gas concentration c. In this method, it suffices to measure only at measurement wavelength $\lambda_{gas}$; a measurement at a reference wavelength $\lambda_{ref}$ is not needed. With regard to the exemplary embodiment of such light emission devices and light detectors, either a broadband infrared light source having a single-channel light detector may be used for realizing this method, i.e., a detector that is only sensitive at measurement wavelength $\lambda_{gas}$, that may be realized by a suitable transmission filter for measurement wavelength $\lambda_{gas}$. Alternatively, a very narrow-band infrared light source, such as an infrared laser or an infrared laser diode, that emits at measurement wavelength $\lambda_{gas}$, and a single-channel light detector (without narrow-band filters for selecting measurement wavelength $\lambda_{gas}$) may be used because the wavelength selection is already given by the specification of the light emitted by the narrow-band light source.

Accordingly, gas sensor device 300 shown in FIG. 3 includes a light emission device 310 that is designed for emitting measurement light of measurement wavelength $\lambda_{gas}$ at a first point in time and at a second point in time into a solid angle region 311 that includes a first and second spatial region 318, 318' which bends outside of gas sensor device 300, and a light detector 380 that is designed for measuring a first intensity $I_1$ of measurement light at, respectively immediately following the first point in time that has been reflected off of a first object 308 located in first spatial region 318 at a first distance 314 from gas sensor device 300, and for measuring a second intensity $I_2$ of measurement light at, respectively subsequently to the second point in time that has been reflected off of a second object 308' located in second spatial region 318' at a second distance 314' from gas sensor device 300.

In addition, as means 1 for determining the length of light absorption path 312, 313, respectively as means for determining the propagation path of the light from light emission device 310 to light detector 380, gas sensor device 300 includes a distance measuring device 390 that is designed for determining distance 314 of first object 308 from gas sensor device 300 at the first point in time, and distance 314' of second object 308' from gas sensor device 300 at the second point in time. In accordance with the exemplary embodiment shown in FIG. 3, distance measuring device 390 is designed as a distance measuring device that is known per se, as is used in cameras, and includes an autofocusing measuring optics 392, that may be driven by a servomotor, for instance, in a controlled or controllable fashion in the direction of distance measurement light beam 356 (illustrated by the double arrow in FIG. 3), and an autofocusing measuring detector 394, that is designed as a flat detector, for example, as a charge-coupled device (CCD) 396. The light from a distance measurement laser 350, which emits a distance measurement light beam 352, 354, 356 of light of a wavelength within the region of visible light or the near infrared, may be used as measurement light for distance measuring device 390 at which the gas mixture, which the light has propagated through, essentially does not absorb any light. The method of functioning of a distance measuring device 390 of this kind is known to one skilled in the art and is not described in greater detail herein.

To measure the light intensities in the infrared spectral region, light emission device 310 includes a broadband light source 340, such as a broadband infrared light diode (IR-LED) that emits measurement light of measurement light wavelength $\lambda_{gas}$ into a solid angle region 311, and, in addition, a beam combiner 370, which, in the exemplary embodiment shown in FIG. 3, is configured as a partially transmitting, essentially plane-parallel plate and is used for superimposing distance measurement light beam 352 emitted by distance measurement laser 350 and light beam 342 emitted by light source 340 to form a mutually superimposed ray bundle in solid angle region 311.

In the case of the measurements performed using two different absorption paths $L_1$ and $L_2$, respectively two different distances 314 and 314' at the temporally offset first and second measurement points in time, two different objects 308, 308' having different distances from gas sensor device 300 may be irradiated by the measurement light. Alternatively, the same object 308 may also be irradiated by the measurement light at the first and the second points in time; however, gas sensor device 300 being displaced, respectively moved relative to reflecting object 308 into a second measuring distance 314' that differs from first measuring distance 314. In accordance with Equation 4, a measured value of the difference between light absorption paths $L_1$ and $L_2$ at the first, respectively second measurement point in time, suffices for calculating molar gas concentration c. The difference between the light absorption paths may be determined in two ways:

- by measuring distance 314, respectively 314', respectively the corresponding propagation paths twice (at the first and second measurement points in time; or
- by using an acceleration sensor, as is currently a standard installation in intelligent cell phones, such as smart phones. In this context, the change in the light absorption path, respectively the change in distance between gas sensor device 300 and object 308 is obtained by a two-times integration of the acceleration measured by the acceleration sensor over the time in the interval from the first to the second measurement point in time.

Light source 340 shown in FIG. 3 is a broadband infrared light source, just as is light source 120 shown in FIG. 1, and is capable of emitting light at measurement wavelength $\lambda_{gas}$ and at reference wavelength $\lambda_{ref}$.

Even when it suffices to provide a single-channel light detector in the case of gas sensor device 300 shown in FIG. 3 to realize the measurement method employing two different distances, light detector 380 shown in FIG. 3 is designed as a two-channel light detector having a first measuring channel 388 for performing light intensity measurements at measurement wavelength $\lambda_{gas}$ and a second measuring channel 389 for performing light intensity measurements at reference wavelength $\lambda_{ref}$. The design and function of light detector 380 corresponds to light detector 180 described with reference to FIG. 1.

This exemplary embodiment also enables gas sensor device 300 shown in FIG. 3 to realize the measuring principle in accordance with Equation 2, respectively in accordance with gas sensor devices 100 and 200 shown in FIGS. 1 and 2, whereby two wavelengths (measurement wavelength $\lambda_{gas}$ and reference wavelength $\lambda_{ref}$) are preferably essentially simultaneously measured.

Light sources 120, 230, 240, 340, 350 used for generating, respectively emitting the measurement light and/or the reference light, may be pulse-operated, whereby they emit short light pulses in regular time intervals. Accordingly, the detector sensitivity may be modulated, or a log-in amplification technique may be used on the detector side in order to eliminate from the calculation the influence of ambient brightness, respectively the halation in the infrared spectral region relevant to the gas absorption measurement. To realize a pulsed operation, the light source may be operated using a variable power supply or, alternatively, a substantially constant power supply and constant optical power; however, what is generally referred to as a shutter device, in particular, a controllable optical shutter device being positioned in the beam path of the light emitted by the light source. A shutter device of this kind is designed for blocking and clearing a transmission path for the light in a controllable temporal sequence. Possible exemplary embodiments of shutter devices of this kind are generally known to one skilled in the art and are not described in greater detail herein.

From Equations 2 and 4, respectively the measuring principles underlying the same for determining molar gas concentration $c[mol/m^3]$, the partial gas pressure and the concentration (in ppm) of the gas to be detected may be calculated using the following known state equation:

$$p*V=n*R*T \quad \text{Equation 5}$$

In this context, p is the pressure, V the volume, T the temperature (expressed in kelvin), and n the number of moles (expressed in molar fractions), and R is the known gas constant, for which it holds that: R=8.3144621, J/(K*mol) expressed in the units J (joule), K (kelvin) and mol (amount of substance). By transposing the equation, respectively by dividing by volume V, an equation is obtained that includes the partial pressure of the gas component to be detected, for instance of $CO_2$:

$$p_{partial}=n/V*R*T=c*R*T \quad \text{Equation 6}$$

Here, $p_{partial}$ is the partial pressure of the gas to be detected, and c is the molar concentration of the gas calculated from equations 2, respectively 6.

Thus, to calculate the partial pressure, temperature T must also be measured. Spatially small temperature sensors, that may be co-integrated in a gas sensor device, are generally known to one skilled in the art and are not described in greater detail herein.

To convert partial pressure $p_{partial}$ of the gas component to be measured, which is determined using Equation 6, to the concentration (expressed in ppm), barometric air pressure $p_{bar}$, thus the barometric pressure of the gas mixture, is still needed. The concentration (expressed in ppm) of the gas to be detected is obtained from the following equation:

$$\text{Conc[ppm]}=p_{partial}/p_{bar}*10^6 \quad \text{Equation 7}$$

The gas pressure of the gas mixture, respectively barometric air pressure $p_{bar}$ may be measured using a separate pressure sensor, which may likewise be integrated in the gas sensor device or be integrated together with the gas sensor device in a small handheld measuring device. It is already frequently the case for an air pressure sensor to be installed in modern cell phones, such as smart phones.

Alternatively to a local measurement, barometric air pressure $p_{bar}$ may be checked using meteorological services, such as those on the Internet. It is then still necessary in some instances to calculate an altitude-pressure compensation in the case that the barometric air pressure queried had been measured at a different elevation above sea level. This could be the case, for example, if the barometric air pressure had been measured at a mountain valley location, and the light absorption and temperature measurement on a mountain near this valley. To compensate for altitude pressure, what is generally referred to as the barometric height formula may be used that is likewise known to one skilled in the art.

Various options are conceivable as means 1 for determining the length of the light absorption path:

Inputting of the light absorption path, respectively the propagation path by an operator;

Using a distance measuring device, for instance, distance measuring device 390 in FIG. 3, such as an auto-focus device in a camera or a camera of a cell phone to estimate or measure the distance. In this case, the infrared measuring light beam is emitted in parallel to the viewing direction of the camera from the light emission device. In addition to the infrared light beam, a light beam having wavelengths in the visible region, for example a laser beam, may be emitted upon which the auto-focus device of the camera may be focused. Even without an additional light beam, respectively without an auto-focus device, an operator may direct the camera, which, for example, is integrated together with the gas sensor device in a housing, at a reflecting object upon which it is possible to effectively focus even using the camera, respectively upon which the image may be sharply focused. By positioning the focus lens, the distance to the object may be estimated, most notably in distance ranges of up to approximately 1 m.

In principle, the distance, respectively the light absorption path, may also be calculated from the measured propagation time of an infrared light pulse. In this context, however, the propagation-time measuring electronics reaches the limits thereof due to the very short propagation times.

The distance to the reflecting object may also be determined in accordance with the technical standard realized in laser distance measurement devices via a frequency modulation and the interference that is thereby measurable in a light sensor. Such a standard is described, for example, in the http address of http://de.wikipedia.org/wiki/Abstandsmessung_%28optisch%29.

The distance to the object may also be separately determined by triangulation; as the case may be, using a separate laser and a camera having an auto-focus device. Such a standard is described, for example, in the http address of http://de.wikipedia.org/wiki/Abstandsmessung#optisch.29.

What is claimed is:

1. A gas sensor device for determining a concentration of a gas to be detected, which gas absorbs light of a measurement wavelength that is characteristic of the gas in an infrared light region, the gas sensor comprising:
   a light detector;
   a light emission device adapted for emitting measurement light of the measurement wavelength (I) into a solid angle region of a light absorption path that extends through the gas to be detected, and (II) to an object that (a) is located outside of the gas sensor device and (b) at least partially reflects the measurement light to the light detector, wherein:
      the light absorption path extends outside of the gas sensor device, from the light emission device to the object, and, by the reflection, from the object to the light detector; and
      the light detector is adapted for measuring an intensity of at least one component of the measurement light that has propagated through the light absorption path; and
   a component configured to determine a length of the light absorption path of the measurement light from the light emission device to the light detector.

2. The gas sensor device according to claim 1, wherein:
   the gas does not absorb light of a predetermined reference wavelength that is in the infrared light region and that differs from the measurement wavelength;
   the light emission device is adapted for emitting the measurement light at the measurement wavelength and the reference light at the reference wavelength into the solid angle region;
   the light detector is adapted for measuring (a) an intensity of the measurement light that has been reflected off of the object, and (b) an intensity of the reference light that has been reflected off of the object.

3. The gas sensor device according to claim 2, wherein the component is configured to determine a propagation path of light from the light emission device to the object and, from the object to the light detector.

4. The gas sensor device according to claim 3, wherein:
   the light emission device is a broadband light source that is adapted for emitting light in a broadband spectral region that includes the measurement wavelength and the reference wavelength; and
   the light detector includes two measuring channels and is adapted for measuring, in a first of the measuring channels, the intensity of the measurement light, which has been reflected off of the object, and for measuring, in a second of the measuring channels, the intensity of the reference light, which has been reflected off of the object.

5. The gas sensor device according to claim 4, wherein the broadband light source includes at least one of a converging lens and a reflector device with an at least substantially concave reflector, the at least one of the converging lens and the reflector being configured to bundle the light emitted from the broadband light source into the solid angle region.

6. The gas sensor device according to claim 4, wherein:
   the first measuring channel of the light detector includes a first filter device that is adapted for transmitting only light that is essentially in a first narrowband measurement spectral region that essentially includes the measurement wavelength and not the reference wavelength; and
   the second measuring channel of the light detector includes a second filter device that is adapted for transmitting only light that is essentially in a second narrowband reference spectral region that essentially includes the reference wavelength and not the measurement wavelength.

7. The gas sensor device according to claim 3, wherein:
   the light emission device comprises:
      a measurement light source adapted for emitting the measurement light in a narrowband measurement spectral region that essentially contains the measurement wavelength and not the reference wavelength; and
      a reference light source adapted for emitting the reference light in a narrowband reference spectral region, that essentially contains the reference wavelength and not the measurement wavelength; and
   the light detector is adapted for measuring the intensity of the measurement light that has been reflected off of the object, and the intensity of the reference light that has been reflected off of the object.

8. The gas sensor device according to claim 3, further comprising:
   an arrangement configured to calculate a molar gas concentration of the gas to be detected based on (a) a ratio of the intensity of the measurement light measured by the light detector and the intensity of the reference light measured by the light detector, and (b) the length of the light absorption path.

9. The gas sensor device according to claim 1, wherein:
   the light emission device is adapted for emitting the measurement light of the measurement wavelength at a first point in time and at a second point in time into the solid angle region;
   the solid angle region encompasses a first and second spatial region located outside of the gas sensor device;
   the light detector is adapted for:
      measuring a first intensity of the measurement light that has been reflected off of a first object located in the first spatial region at a first distance from the gas sensor device at or subsequent to the first point in time; and
      measuring a second intensity of the measurement light that has been reflected off of a second object located in the second spatial region at a second distance from the gas sensor device at or subsequent to the second point in time; and
   the component is configured to determine a difference between (a) a first propagation path of the light that extends from the light emission device to the first object and, from the first object to the light detector, and (b) a second propagation path of the light that extends from the light emission device to the second object and, from the second object to the light detector.

10. The gas sensor device according to claim 9, further comprising:
    an arrangement configured to calculate a molar gas concentration of the gas to be detected based on (a) a ratio of the first intensity of the measurement light measured by the light detector that has traversed the first propagation path, and the second intensity of the measurement light measured by the light detector that has traversed the second propagation path, and (b) the difference between the first propagation path and the second propagation path.

11. The gas sensor device according to claim 1, wherein the light emission device is adapted for emitting light in one or more light pulses.

12. The gas sensor device according to claim 1, wherein the component configured to determine the length of the light absorption path is selected from a group which includes the following:
   an input device adapted for inputting a distance between the gas sensor device and the object that corresponds to the propagation path, or for inputting the propagation path by an operator of the gas sensor device;
   a distance measuring device adapted for generating a signal that is indicative of the distance between the gas sensor device and the object that corresponds to the propagation path, the distance measuring device including an auto-focus device of a camera;
   a component adapted for determining the propagation path of the light emitted by the light emission device in a form of light pulses, based on a measurement of propagation time of at least one light pulse;
   a laser distance measurement device adapted for determining the distance based on a frequency modulation of light emitted by a laser light source and an interference produced by the light; and
   a triangulation device that includes a laser device that is provided separately for the gas sensor device, and a camera that is mechanically coupled to the gas sensor device.

13. The gas sensor device according to claim 1, further comprising:
   a pressure sensor adapted for measuring barometric air pressure; and
   an arrangement adapted for determining a concentration of the gas to be detected based on a specific molar concentration of the gas and the barometric air pressure measured by the pressure sensor.

14. The gas sensor device according to claim 1, wherein the gas sensor device is an integrated part of a portable device, a cell phone, a camera, a handheld measuring device, or a laser distance measurement device.

15. A method for determining, by a gas sensor device, a concentration of a gas to be detected, which gas absorbs light of a measurement wavelength that is characteristic of the gas in an infrared light region, the method comprising:
   emitting, by a light emission device, measurement light of the measurement wavelength (I) into a solid angle region of a light absorption path extending through the gas to be detected and (II) to an object that (a) is located outside of the gas sensor device and (b) at least partially reflects the measurement light to a light detector, wherein the light absorption path extends outside of the gas sensor device, from the light emission device to the object, and, by the reflection, from the object to the light detector;
   measuring, by the light detector, an intensity of at least one component of the measurement light that has propagated through the light absorption path; and
   determining a length of the light absorption path of the measurement light from the light emission device to the light detector.

* * * * *